United States Patent [19]

Barfield

[11] Patent Number: 4,603,442
[45] Date of Patent: Aug. 5, 1986

[54] SINGLE LENS GOGGLE

[76] Inventor: Kenneth E. Barfield, 1283 E. South Temple, Salt Lake City, Utah 84102

[21] Appl. No.: 687,572

[22] Filed: Dec. 28, 1984

[51] Int. Cl.$^4$ .................................................. A61F 9/02
[52] U.S. Cl. ............................................. 2/447; 2/446
[58] Field of Search ............... 2/439, 427, 431, 432, 2/434, 435, 436, 437, 440, 441, 452, 447

[56] References Cited

U.S. PATENT DOCUMENTS

| | | | |
|---|---|---|---|
| 2,296,634 | 9/1942 | Fink | 2/447 |
| 3,791,722 | 2/1974 | Ahlberg et al. | 2/447 X |
| 3,952,331 | 4/1976 | Melville | 2/431 |
| 4,101,980 | 7/1978 | Stepan et al. | 2/434 X |
| 4,176,410 | 12/1979 | Matthias | 2/439 X |
| 4,367,561 | 1/1983 | Solari | 2/439 |
| 4,447,914 | 5/1984 | Jannard | 2/432 |

FOREIGN PATENT DOCUMENTS 2732398  2/1979  Fed. Rep. of Germany .......... 2/452

Primary Examiner—Peter Nerbun
Attorney, Agent, or Firm—Mallinckrodt & Mallinckrodt

[57] ABSTRACT

A single lens safety goggle for use during athletic play to protect a wearer's eyes and portions of their face from injury as could be incurred by a ball or racket striking thereon. The single lens is formed from a shatter proof plastic material having good optical qualities that is maintained across a wearer's face by a strap arrangement and includes, to support the goggle to the wearer's face, a nose bridge mount and removable pad therefor and temple posts and removable pads therefor are provided, the mount, posts and pads all formed of a soft flexible material. The respective pads are easily removable for squeezing water therefrom or replacement and preferably include, on at least one face thereof, a moisture adsorbing surface for engaging the wearer's face.

14 Claims, 4 Drawing Figures

SINGLE LENS GOGGLE

BACKGROUND OF THE INVENTION

1. Field

This invention relates to safety goggles, and more particularly, to safety goggles for use when participating in sporting activities.

2. General

In a number of sporting activities, particularly those involving play with racquets such as squash, racquetball, tennis and the like, and even in sports activities that do not involve racquets such as handball, basketball, and soccer, for example, there is an ever present danger of a participant being struck in the eye by a ball, a racquet, or the hand of his opponents, potentially resulting in a devastating injury. The wearing of eye protection devices, particularly for sports played in close quarters, such as a squash or racquetball court, is therefore essential for the health and well being of the participants. Where heretofor such eye protection devices have ranged from screens or bars maintained in frames to plastic lens glasses mounted in shock resistant mountings and the like, none have provided a versitile and useful single lens structure like that of the present invention.

3. Prior Art

Goggles and like apparatus that include horizontally disposed eye openings or a single lens structure that is support for arrangement across a wearer's central sight zone for use in athletic activities have gained in use with an increased popularity of racquet sports. One such arrangement of a safety goggle is shown in a U.S. Pat. by Solari, No. 4,229,837 that involves a frame for close fitting around a wearer's head with lensless openings. The goggles include open eye shields with tooth edges that project towards the individual goggle open center or, alternatively, bars or the like can be arranged thereacross. All of the configurations of the Solari Patent are for prohibiting entry of a ball or the edge of a racquet to strike a wearer's eye. Typical for this kind of safety goggles, the Solari Patent shows resilient pads permanently fixed to the inner frame surface proximate to the wearer's temples as well as a pad secured to the frame bridge for contacting the wearer's nose and extending vertically somewhat therebeyond, the resilient pads providing a cushioning against a blow on the goggles as a wearer would experience if they were to be hit by a ball or racquet.

Similar to the arrangement of the Solari Patent, the present invention also involves pads that are strategically positioned proximate to the wearer's respective temples and from his nose bridge area to mid forehead. These pads, however, are distinct in that they are easily removable in that they are arranged to function in cooperative relationship to flexible posts and a flexible nose bridge mount which are secured to the goggle lens. Where pads capable of adsorbing moisture or sweat from a wearer's face are not new, pads of the present invention arranged to be removable for washing or replacement are believed to be. An example of a sweat adsorbing member is shown in a patent by McNeill, U.S. Pat. No. 2,271,703, that includes a sweat adsorbing headband. Such headband, while it provides for cushioning in addition to adsorbing moisture is not for supporting the goggle to the wearer's face as does the present invention. Also, where the McNeill Patent does show a frame with channels formed therein for receiving sweatband sections, it does not involve the combined soft and flexible nose bridge mount with channel formed therein and temple pad post for mounting removable sponge temple and nose bridge pads of the present invention.

The above cited Solaris and McNeill Patents are goggle arrangements each employing separate lenses unlike the single lens goggle of the present invention. Single lens goggles are shown in patents by Ahlberg et al., U.S. Pat. No. 3,791,722; and Malcom Jr., U.S. Pat. No. 2,563,125, but are otherwise structurally and functionally unlike the present invention. The Ahlberg U.S. Pat. No. 3,791,722, unlike the present invention, involves, essentially, a continuous perimeter cushion, the lens supported therearound. The Macolm Jr. Patent is directed to a support brace to maintain a lens in spaced apart relationship from the wearer's face to provide a free flow of air therethrough and is not intended as a device for cushioning or dampening a shock applied thereagainst as by an object striking the lens surface. While, the support bar thereof may be covered with a suitable cushioning material, such will not adsorb a force applied thereon and is merely to comfortably position the goggle arrangement on the wearer's forehead.

Other patents by Janz, U.S. Pat. No. 3,133,982; De Angelis, U.S. Pat. No. 3,233,956; and Lindblom, U.S. Pat. No. 3,391,976 all involve goggle arrangements that show various sweatband, cushioning, and support arrangements but are unlike the present invention. The Janz Patent involves a glue or stick on type sweatband section for use with conventional glasses extending across a wearer's brow area. This section, while it could adsorb some shock and will, of course, provide for sweat or moisture adsorption, is not for use in conjunction with a contoured channel and in fact could not be easily removed and reused after a washing or after squeezing moisture therefrom as the glue layer probably could not be used to reattach the sweatband section to the glasses frame. The section and its attachment arrangement is distinct from the contoured channel and removable pad for installation therein of the present invention. The De Angelis Patent involves a nose bridge cushion for releasable attachment to a glasses frame and is provided to distribute the weight of the eye glasses over a greater nose area. Similarly, the Lindblom Patent shows also a nose piece for releasable attachment to a glasses frame that is also for distributing weight therefrom and would not provide for an effective distribution of an impact force should the glasses be struck at other than the nose bridge itself.

SUMMARY OF THE INVENTION

It is the principal object of the present invention in a safety goggle to provide a single lens goggle, which single lens is constructed from an unbreakable polycarbonate, or like plastic material having good optical properties that is arranged to bend across the nose bridge area to conform to a wearer's head and includes sponge nose bridge and temple pads that are removable for cleaning or replacement.

Another object of the present invention in a safety goggle is to provide removable nose bridge and temple pads for arrangement therewith for cushioning and spacing apart the lens off from the wearer's face that are arranged to be water adsorbing or have water adsorbing layers therewith, which pads can be easily wrung out, replaced and are washable.

Another object of the present invention in a safety goggle is to provide soft and flexible mounts for securing the removable nose bridge and temple pads thereto, providing an interference or friction fit therebetween.

Still another object of the present invention is to provide a safety goggle where the single lens is configured to extend across the wearer's face, covering the wearer's eyes and over the cheekbones that will bend at the lens vertical center at the wearer's nose bridge area to conform to that wearer's face and will provide distortion free field of vision therethrough.

In accordance with the above objects, the present invention is in a single one piece lens goggle that includes strap attachment slots formed in opposite ends thereof which lens is shaped to cover the wearer's eyes and lower forehead area, extending to the cheekbone area, tapering inwardly at the vertical center thereof at the nose bridge area. The lens is thereby weakened at the center to allow for a uniform bending to bring pads arranged at the lens ends into engagement with opposite sides of a wearer's face at their temples. The lens is formed of a strong, unbreakable material such as a polycarbonate to provide a distortion free field of vision therethrough. A preferred strap for installation through the strap slots to maintain the lens to a wearer's head is one formed of a conventional stretch fabric and is adjustable to fit the wearer's head.

The lens includes, secured across the center area thereof, a nose bridge mount that is formed of a soft flexible material to extend vertically between and somewhat beyond the lens at the center thereof, the mount upper portion having a gull wing shaped channel or slot formed therein to accommodate a nose bridge pad that is shaped to fit therein. The mount at the lower end thereof is split into legs that are angled oppositely from the vertical to form an inverted V that will rest on the bridge of a wearer's nose. The nose bridge mount and nose bridge pad are preferably formed of a same soft flexible foam material and the nose bridge pad can further include, on one or both faces, a section of a soft adsorbant material such as a velour bonded thereto to engage the wearer's skin. The nose bridge pad has a complementary shape to closely fit within the gull wing shaped channel forming an interference or friction fit within that channel, and can be easily removed for squeezing water therefrom, for washing by conventional means, or for ease of replacement.

The goggle further includes temple pads and mountings therefore. The preferred mountings consist of flexible posts that are secured to opposite ends of the lens, opposite the wearer's temple area. The posts are identical, each preferably formed as a long rectangular section that is fixed to the individual lens end area to stand outwardly from the lens surface each to fit through a hole formed through a separate temple pad. The nose bridge mount and pad, the posts and the temple pads are all preferably from the same soft flexible foam material. The temple pads each accommodate one of the posts fitted therethrough providing an interference or friction fit. The temple pads like the nose pad can include on one or both faces a soft adsorbant material such as a velour to engage the wearer's face. The temple pads are contoured appropriately to support the lens ends to the wearer's face and to protect the wearer's temple areas. The temple and nose bridge pads are easily removable for squeezing water therefrom, or for replacement.

BRIEF DESCRIPTION OF THE DRAWINGS

These and other objects will appear in the following detailed description in which the preferred embodiment of the invention will be described in detail in conjunction with the accompanying drawings.

DETAILED DESCRIPTION

Referring now to the Drawings

Figure 1:
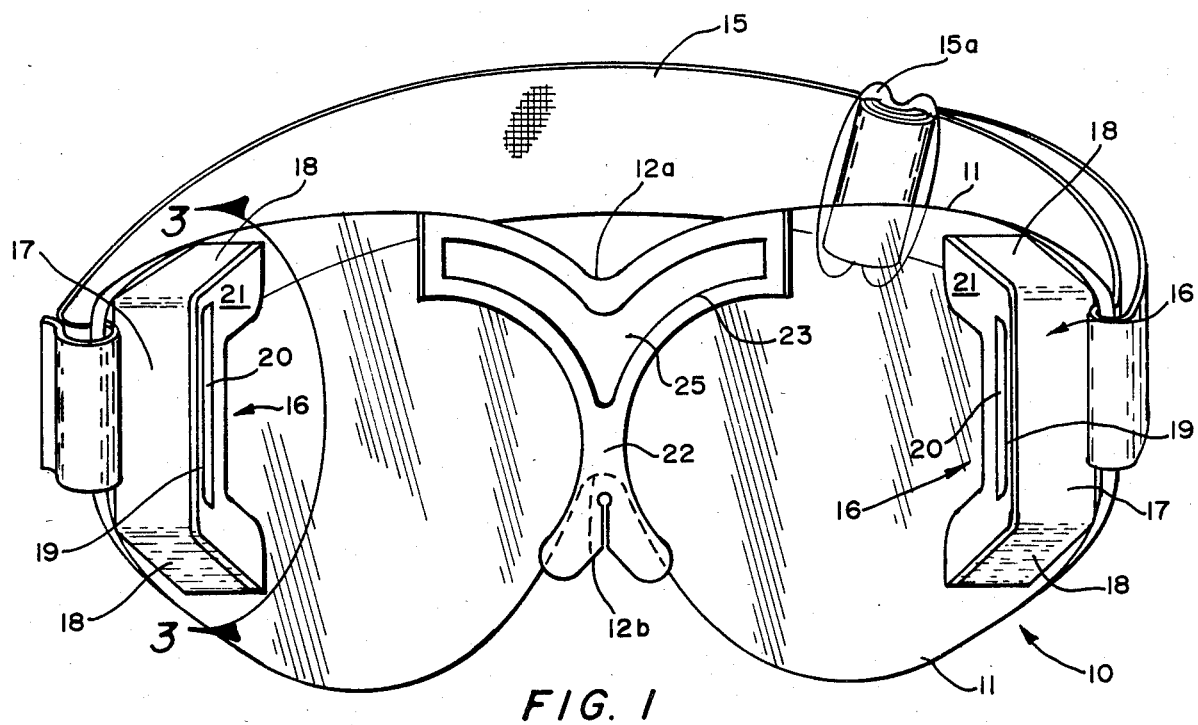
FIG. 1, is a perspective view of the goggle of the present invention.
Figure 4:
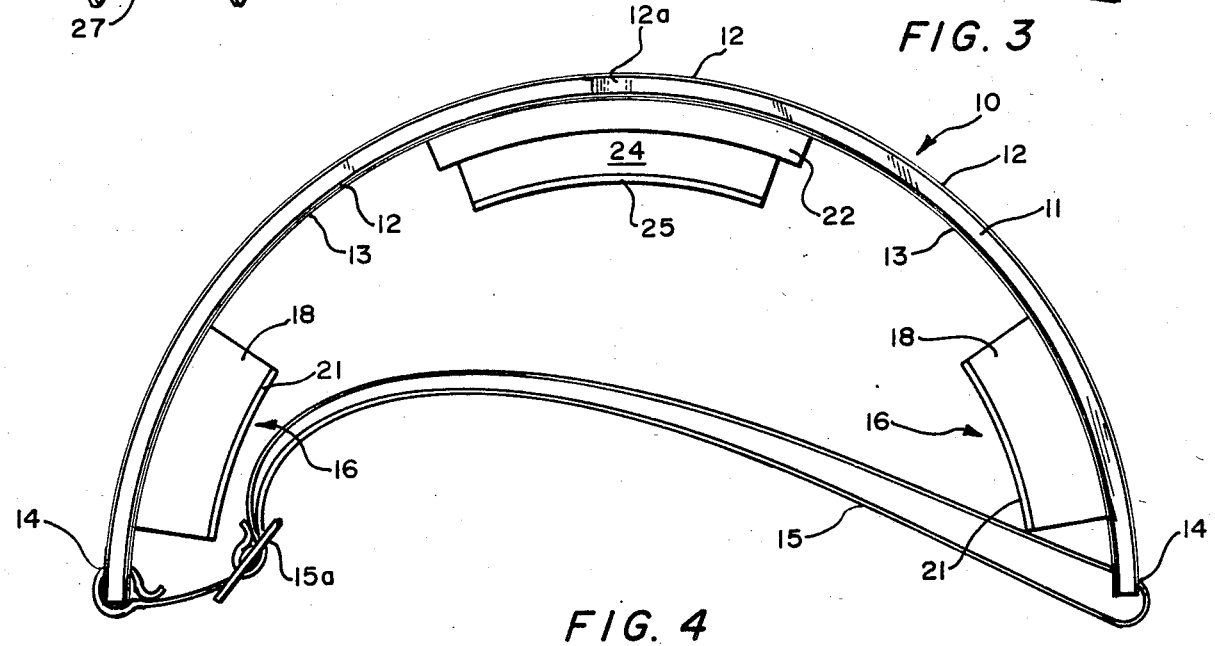
FIG. 4, is top plan view of the goggle of FIG. 1.

In FIG. 1 is shown a perspective view of a single lens safety goggle 10 of the present invention, hereinafter referred to a goggle as it would appear to a person preparing to place the goggle over their head. The goggle includes a one piece shatter resistant or unbreakable lens 11, hereinafter referred to as lens, that is preferably constructed of a fairly rigid polycarbonate or from some other equally rigid and unbreakable plastic material having good optical properties that can be tinted or colored appropriately as described. Shown best in FIG. 4, lens 11 is preferably coated on opposite faces with a material that will form a scratch resistant surface thereover. Shown in FIG. 4, a coating 12 has been applied to both lens faces, that provides a scratch resistant surface thereto. Of course, such coating is optional and/or need only be applied to one face or the other. Some commercially available materials for providing such hard surface coatings include a CTG Sheet, manufactured by General Electric, a liquid coating identified as Abrasion Resistant Coating manufactured by Dow Chemical, and a liquid coating identified as Exxene Hard Coat, manufactured by Exxene. Additionally, within the scope of this disclosure, the invention may include, on the inner lens face, an anti-fog agent coating 13.

Figure 3:
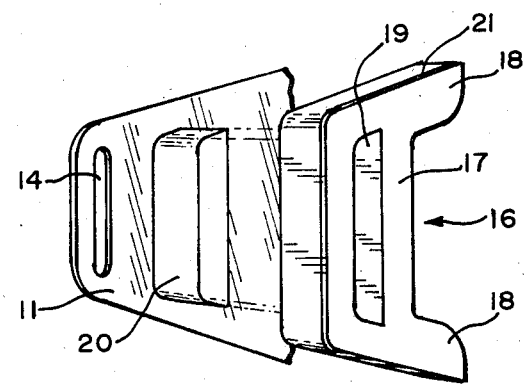
FIG. 3, is a perspective view taken within the line 3—3 of FIG. 1 showing a temple pad exploded away from a flexible post that is secured to the goggle lens end.

As shown best in FIG. 1, the goggle lens 11 is formed to provide coverage to the areas of the wearer's face that would be most susceptable to injury. Specifically, the eye socket area with the lens preferably extending therefrom down over a wearer's cheekbones. Preferably, the lens is rounded outwardly from the vertical center to a wearer's cheekbones and to the wearer's brow area, tapering therefrom to a lesser width or distance thereacross at the lens ends. The lens ends, as shown in FIGS. 1 and 3, each include an elongate slot 14 formed therethrough to receive a strap 15. The strap is threaded therethrough and through a buckle, 15a or like arrangement, for adjusting the strap length to accommodate a wearer's head size. As illustrated best in FIG. 1, the goggle lens 11 curves inwardly at a vertical center to recessed areas 12a and 12b at the wearer's brow center and nose bridge area, respectively, shortening the distance between the lens opposite edges at the lens vertical center to promote a desired bending thereacross when the lens ends are drawn into proximity with the wearer's head at their temple areas. To support and space apart the lens surface from the wearer's face a removable temple pad 16 is provided at each of the wearer's temples that, as shown in FIGS. 1 and 3, is for installation alongside the headband slots 14, with the opposite sides of each pad approximately aligning with the lens 11 edges. Each temple pad 16, as shown in FIG. 3, is preferably formed of a soft foam material that is resilient and should be of a sufficient thickness such that, even when compressed, it will cause the lens to stand off a desired distance from the wearer's face to permit an airflow to pass freely over the lens inner face, discouraging lens fogging. In practice, a three eights to one half inch thickness is preferred for the temple pads, which foam material of the same thickness is preferred for a nose bridge pad as discussed herein below. Some preferred foams that have been and can be used in practice are an ethylene vinyl acetate foam, an olefinic foam, or a nitrile rubber PVC blend foam. Examples of such foams are: Beva manufactured by (General or Monarch Foam Corp.); or Ensolite, manufactured by (Uniroyal).

Each temple pad 16 is preferably formed to have a spread U shape, the center or web 17 thereof being thick and essentially straight to extend vertically across the lens end. From the web ends legs 18 extend outwardly and are angled apart towards the nose bridge area or lens center, the sides of each leg essentially parallel to one another and outer edges of each leg essentially aligning with the adjacent lens 11 edge. An elongate opening 19 is provided through each pad web 17, the opening approximately centered, extends longitudinally thereacross and has dimensions to fit closely over a post 20 that is secured, as illustrated in FIG. 3, to extend outward from and at essentially a right angle to the lens inner face, proximate to and essentially parallel to the adjacent lense elongate slot 14. Post 20 is preferably formed from the same soft resilient material as are the temple pads 16 and will compress against the wearer's temple area. In practice, the post 20 and a bridge pad mount 22 are formed from the same material as are the temple pads 16 and a nose bridge pad 24, the nose bridge mount and pad described hereinbelow with respect to FIG. 2. The materials of the pads and posts as set out above are preferaby formed from the same material though they could be formed of different materials provided such materials are each soft and flexible. Additionally, each temple pad 16 preferably includes a moisture absorbing or wicking surface 21 that is installed to contact a wearer's face. A section of velour has been found in practice to work effectively as the wicking or moisture absorbing surface and it preferably bonded to the temple pad 16 by an adhesive that is capable of maintaining, during flexing, the fabric and porous sponge surfaces together. Additionally, where a wicking surface is shown herein bonded to one face of each temple pad 16 and nose bridge pad 24 only, it should be understood that both faces of the pads can receive a wicking surface fixed thereto within the scope of this disclosure. The temple pads 16 are, of course, essentially duplicates of one another and are mounted, as described, such that the sides 18 are angled inwardly towards the goggle center or bridge area, and therefore the above description for the one temple pad should be taken as a description of the other also.

Figure 2:
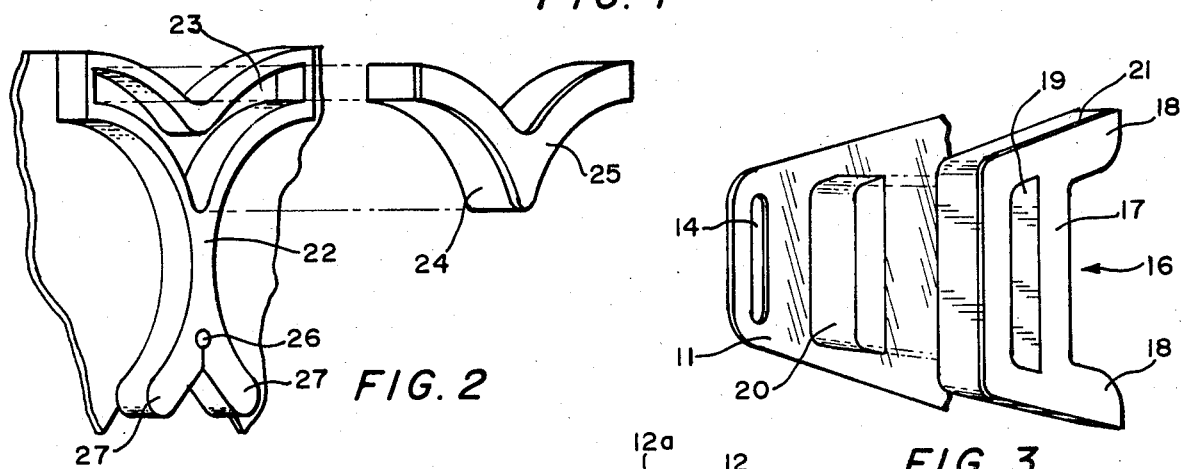
FIG. 2, is a perspective view of a broken away section of the goggle of FIG. 1 center showing a nose bridge mount with a nose bridge pad shown exploded away.

Shown best in FIG. 1 and in the exploded sectional view of FIG. 2, the goggle 10 includes for support and cushioning the nose bridge mount 22 that both engages and supports the goggle on a wearer's nose at the nose bridge area and provides a track or channel for receiving a nose bridge pad therein. The nose bridge mount 22 is formed to extend across the lens center between the opposite recesses 12a and 12b formed therein and includes a channel 23 that is formed across a top or upper end to be opposite to a wearer's forehead area. The channel 23 has an open area formed therethrough to have essentially, a gull wing shape to accommodate the nose bridge pad 24 installed therein. As set out above, the nose bridge pad is preferably formed from the same material as are temple pads 16 and preferraby also includes a velour cloth section or layer 25, or a like wicking or moisture adsorbing surface, bonded to one or both faces to engage a wearer's forehead when the pad is installed in the channel 23. The nose bridge pad 24 to fit snuggly therein, will have a shape that is like the gull wing shaped channel 23 such that when it is installed therein, an interference or friction fit will be created. As set out above, the soft flexible material wherefrom the nose bridge mount 22 is formed is preferably the same as that used to fabricate the temple posts 20, and, like temple posts 20, the nose bridge mount is also preferably bonded to the lens, extending across the vertical center area thereof, by an adhesive. Nose bridge mount 22, on its end opposite to the gull wing shaped channel 23, as shown best in FIG. 2, is split vertically to 26 forming legs 27, which legs are angled oppositely from the vertical, forming an inverted V to accommodate the bridge of a person's nose fitted into the open area between the V legs. To position the goggle 10 over a wearer's eyes, the strap 15 fitted around the wearer's head, the nose bridge mount 22 is balanced on the bridge of the wearer's nose between legs 27, the material thereof compressing appropriately to provide a snug and comfortable fit, with the nose bridge pad 25 and temple pads 16 also compressed against the wearer's forehead and temple areas. The goggle 10, as set out above, with the two removable temple pads 16 and the nose bridge pad 25 provides a three point support system for suspending the goggle off the wearer's face a sufficient distance to encourage an airflow therethrough so as to discourage lens fogging during active play by wearer. All of which pads are easily removed and reinstalled for ease of squeezing water therefrom, washing, or replacement, with, in addition, when velour surfces bonded to both temple and nose bridge pad faces, the pads can be removed during play to replace a wet skin engaging surface with a dry one.

While a preferred embodiment of the single lens goggle 10 of the present invention has been shown and described hereinabove, it should be understood that the present disclosure is made by way of example only and that any departure from the described elements and their interaction are possible without the departing from the subject matter coming from the scope of the following claims, which claims I regard as my invention.

I claim:

1. A single lens goggle comprising, a single lens formed from a clear shatter resistant plastic material adapted to cover a wearer's eye socket areas extending to and over the wearer's temple areas, said lens being shaped to encourage bending across a vertical center thereof; means for securing a strap means to said lens ends to maintain the goggle across the wearer's face; a nose bridge mount means formed from a soft flexible material secured to said lens across the vertical center thereof and formed to provide a nose bridge engaging rest on one end thereof with a nose bridge pad receiving channel formed in the other; a nose bridge pad formed from a soft flexible material to have a shape that conforms to said nose bridge mount channel internal dimensions to form an interference fit of said pad within said channel so as to be removably mounted in said channel; temple pad mount means formed from a soft flexible material that are secured to said lens, one mount to each lens end area; and temple pads, each formed from a soft flexible material that are each shaped to cover a goggle wearer's temple area providing a lens support point at each temple area, each pad including a hole formed therethrough to receive one of said temple pad mounts fitted therein forming a interference fit so as to be removably mounted on said temple pad mounts.

2. A single lens goggle as recited in claim 1, wherein the lens is formed from a polycarbonate material.

3. A single lens goggle as recited in claim 1, further including coating at least one lens face with a material to form a scratch resistant surface thereover.

4. A single lens goggle as recited in claim 1, wherein the means for securing a strap means are vertical slots formed through the lens ends wherethrough said strap means is threaded.

5. A single lens goggle as recited in claim 1, wherein the nose bridge mount is split at the lower end into legs that are oppositely angled from the vertical to form an inverted V to accommodate the bridge of a wearer's nose therebetween.

6. A single lens goggle as recited in claim 5, wherein the nose bridge pad receiving channel is formed as an opening through said nose bridge mount upper end to have a gull wing shape, and the nose bridge pad is formed to have a like gull wing shape to fit snuggly in said channel.

7. A single lens goggle as recited in claim 5, wherein the nose bridge mount, the nose bridge pad, the temple pad mount means and temple pads are all formed from the same soft flexible material.

8. A single lens goggle as recited in claim 1, where the nose bridge pad further includes a section of a moisture adsorbent material secured to at least one face thereof for engagement with a goggle wearer's face.

9. A single lens goggle as recited in claim 8, wherein the moisture absorbent material is a velour.

10. A single lens goggle as recited in claim 1, wherein each temple pad mount means is formed as an elongate post that is bonded to the lens to extend outwardly at essentially a right angle thereto and is centered vertically.

11. A single lens goggle as recited in claim 10, wherein the temple pads are each formed to have a wide U shape, the web thereof having an elongate hole formed therethrough to receive a temple pad mount means fitted therein, the temple pads each including legs that extend from each web end and are angled oppositely to one another from the horizontal, the outer edges of each said leg essentially aligning with an adjacent lens edge.

12. A single lens goggle as recited in claim 1, further including a section of a moisture absorbent material secured to at least one face of each of the temple pads for engagement with a goggle wearer's face.

13. A single lens goggle as rectied in claim 12, wherein the moisture absorbent material is a velour.

14. A single lens goggle comprising, a single lens formed from a clear shatter resistant plastic material adapted to cover a wearer's eye socket areas extending to and over the wearer's temple areas, said lens being shaped to encourage bending across a vertical center thereof; means for securing a strap means to said lens ends to maintain the goggle across the wearer's face; a nose bridge mount means formed from a soft flexible material secured to said lens across the vertical center thereof and formed to provide a nose bridge engaging rest on one end thereof with a nose bridge pad receiving channel formed in the other; a nose bridge pad formed from a soft flexible material to have a shape that conforms to said nose bridge mount channel internal dimensions to form an interference fit of said pad within said channel; temple pad mount means formed as elongate posts from soft flexible material, each post being bonded to said lens at an end area to extend outwardly at essentially a right angle to said lens and being centered vertically thereon; and temple pads of wide U shape configuration, each formed from soft flexible material and shaped to cover a goggle wearer's temple area providing a lens support point at each temple area, the web thereof having an elongate hole formed therethrough to receive a temple pad mount means fitted therein for an interference fit, the temple pads each including legs that extend from each web end and are angled oppositely to one another from the horizontal, the outer edges of each said leg essentially aligning with an adjacent lens edge.

* * * * *